(12) United States Patent
Zielinska et al.

(10) Patent No.: US 9,033,903 B2
(45) Date of Patent: May 19, 2015

(54) TRI-AXIAL ELECTRO-GONIOMETER FOR SPINAL MOTION, ASSOCIATED SYSTEM AND METHODS

(71) Applicant: The Trustees of the Stevens Institute of Technology, Hoboken, NJ (US)

(72) Inventors: Justyna Zielinska, Linden, NJ (US); Samantha Music, Wayne, NJ (US); Kerri Killen, Cranford, NJ (US); Antonio Valdevit, Effort, PA (US); Colin Harris, Syracuse, NY (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 136 days.

(21) Appl. No.: 13/800,229

(22) Filed: Mar. 13, 2013

(65) Prior Publication Data

US 2014/0018704 A1    Jan. 16, 2014

Related U.S. Application Data

(60) Provisional application No. 61/670,963, filed on Jul. 12, 2012.

(51) Int. Cl.
| | |
|---|---|
| *A61B 5/117* | (2006.01) |
| *A61B 5/103* | (2006.01) |
| *A61B 5/11* | (2006.01) |
| *A61B 5/00* | (2006.01) |

(52) U.S. Cl.
CPC ............. *A61B 5/1121* (2013.01); *A61B 5/4566* (2013.01); *A61B 5/0022* (2013.01); *A61B 5/7246* (2013.01); *A61B 5/1126* (2013.01)

(58) Field of Classification Search
USPC ................... 600/587, 592, 594, 595; 434/252
See application file for complete search history.

(56) References Cited

U.S. PATENT DOCUMENTS

| | | | |
|---|---|---|---|
| 4,971,069 | A | 11/1990 | Gracovetsky |
| 5,143,088 | A | 9/1992 | Marras et al. |
| 5,146,929 | A | 9/1992 | Sawhill |
| 5,337,758 | A | 8/1994 | Moore et al. |
| 5,400,800 | A | 3/1995 | Jain et al. |
| 5,640,971 | A | 6/1997 | Martin, Jr. |
| 5,772,610 | A | 6/1998 | McGorry et al. |
| 5,826,578 | A * | 10/1998 | Curchod ........................ 600/595 |
| 5,989,201 | A | 11/1999 | Brunner |
| 6,673,027 | B2 * | 1/2004 | Fischer .......................... 600/595 |
| 7,431,703 | B2 | 10/2008 | Salvi et al. |
| 2006/0030793 | A1 * | 2/2006 | Granata et al. ................ 600/592 |
| 2006/0036151 | A1 | 2/2006 | Ferre et al. |

* cited by examiner

*Primary Examiner* — Brian Szmal
(74) *Attorney, Agent, or Firm* — Greenberg Traurig LLP

(57) ABSTRACT

A goniometer has three potentiometers with axes of rotation that intersect at a point for measuring angular range of motion of an anatomy, such as of the spine or jointed appendages. The intersecting axes facilitate calculation of angle based on potentiometer output and allow the rotations on each of the three axes to be measured independently and simultaneously without mechanical or electrical cross talk. The angular measurements may be recorded on a computer for analysis and playback and may be continuously captured over a range of motion. The captured data may be compared to samples from the same person or others to aid in assessment of function.

22 Claims, 11 Drawing Sheets

TRI-AXIAL ELECTRO-GONIOMETER FOR SPINAL MOTION, ASSOCIATED SYSTEM AND METHODS

CROSS-REFERENCE TO RELATED APPLICATIONS

The present application claims the benefit of U.S. Provisional Application No. 61/670,963, filed on Jul. 12, 2012, entitled TRI-AXIAL ELECTRO-GONIOMETER FOR SPINAL MOTION, the disclosure of which is incorporated herein by reference in its entirety for all purposes.

FIELD OF THE INVENTION

The present disclosure relates to biomedical engineering, and, more particularly, to a goniometer for the measurement of spinal motion.

BACKGROUND OF THE INVENTION

Currently, surgeons will take approximately six x-rays of a patient's spine during both a pre-operative visit, as well as, at least three post-operation visits in order to determine spinal motion. These x-rays are not cost efficient for the patient, as the total is about $2000 per visit. The exposure to radiation is also harmful for the patient, as it is 60 mrem per x-ray. Each x-ray taken is time consuming and requires the patient to stand still while the series of x-rays are taken during each visit. Alternative apparatus and techniques for measuring spinal motion without the use of x-rays are therefore desirable.

SUMMARY OF THE INVENTION

An embodiment of the present disclosure features a device for measuring movement of a body having a first point that is moveable relative to a second point and includes a plurality of mechanically coupled articulable elements capable of rotating relative to one another, establishing a plurality of axes of rotation and defining an articulable assembly. A sensor is coupled to at least one of the articulable elements and is capable of sensing rotation thereof relative to an adjacent articulable element and generating a first signal representative of the angle of rotation. A computer communicatively coupled to the sensor is capable of receiving a signal corresponding to the first signal and storing the angle of rotation. A first end of the articulable assembly is capable of coupling proximate the first point on the body. A second end of the articulable assembly is capable of coupling proximate to the second point on the body.

In another embodiment, the axes are three in number.

In another embodiment, the three axes intersect.

In another embodiment, the rotation of any of the articulable elements on the three axes is independent of the rotation of any other of the articulable elements.

In another embodiment, the articulable assembly is capable of simultaneous independent movement of each of the plurality of articulable elements when moved by the body, generating a plurality of independent signals attributable to rotation about the three axes.

In another embodiment, the plurality of sensors are three in number, one each for monitoring rotation about one of the three axes.

In another embodiment, the sensors are potentiometers.

In another embodiment, the potentiometers each have a stem rotatable relative to a housing thereof, the potentiometers forming the mechanical link between adjacent elements in the articulable assembly upon which the adjacent elements pivot, with the stem attached to a first of the adjacent elements and the housing attached to a second of the adjacent elements, the potentiometers capable of generating the first signal when rotated.

In another embodiment, the device includes an interpreter capable of receiving the first signal, converting it to a digital signal and conveying the digital signal to the computer.

In another embodiment, the computer has a program running therein capable of converting the digital signal into rotational angle data corresponding to the rotation of the articulable elements and communicating the angle data to a user.

In another embodiment, the angle data stored in the computer is obtained over a period of time at a given sampling rate, such that multiple angle data values are generated and stored when the body executes a motion from a first position to a second.

In another embodiment, the interpreter includes a Wheatstone bridge for determining a resistance value of the potentiometer at a given rotational position of the potentiometer.

In another embodiment, the device includes a first extension with a first end coupled to the first end of the articulable assembly and a second end capable of being coupled to the body proximate the first point and a second extension with a first end coupled to the second end of the articulable assembly and a second end capable of being coupled to the body proximate the second point.

In another embodiment, the device includes a wireless connection between the device and the computer.

In another embodiment, the computer is connected to the Internet and is capable of communication the signal data to a remote computer.

In another embodiment, the device includes a phone interface through which the angle data may be communicated to another over a wireless network.

In another embodiment, the articulable assembly includes a U-shaped flange, two L-shaped flanges and a coupling intermediating there between, a first potentiometer attached to a first arm of the U shape by the housing thereof with the stem thereof extending toward and being mechanically coupled to a first arm a first of the L-shaped flanges, a second potentiometer attached a second arm of the first L-shaped flange with the stem thereof extending toward and mechanically coupled to the coupling, a third potentiometer attached to a first arm of the second L-shaped flange with the stem thereof extending toward and mechanically coupled to the coupling at right angles to the stem of the second potentiometer, the first end of the first extension attached to the U-shaped flange at a second arm opposite to the first potentiometer and the first end of the second extension attached to the second L-shaped flange on a second arm of the second L-shaped flange, the second ends of the first and second extensions capable of being coupled to a harness worn on the body.

In another embodiment, a method of measuring the movement of an articulable anatomy moveable from a first position to a second position, includes the steps of:
(A) obtaining a goniometer with an articulable assembly having a plurality of articulable elements rotatable about a plurality of intersecting axes and sensors capable of generating signals representative of the rotation of the articulable elements about the axes;
(B) coupling the goniometer to the anatomy, with the goniometer bridging from a first point on the anatomy to a second point on the anatomy, such that when the anatomy moves, the first point moves relative to the second point and moves the articulable elements in a manner corresponding to the movement of the anatomy, the sensors generating virtually simultaneous, independent signals corresponding to each rotational movement of the articulable elements;
converting the independent signals into angle data representing the magnitude of rotation sensed by each sensor and;
recording the angle data for a plurality of movement states from a start position of the anatomy to an end position.

In another embodiment, the axes are three in number and further comprising the step of comparing the angle information to angle information previously obtained during the motion of a comparable anatomy.

In another embodiment, the anatomy is a spine.

In another embodiment, the anatomy is an articulable appendage.

In another embodiment, the measuring is conducted to assess the functionality of the anatomy and includes the step of comparing a first set of angle data associated with the anatomy to a second set of angle data associated with a comparable anatomy executing a similar motion pattern at an earlier time.

In another embodiment, the comparable anatomy is the anatomy of the same individual.

In another embodiment, the comparable anatomy is the anatomy of at least one other individual.

In another embodiment, the device includes a linear transducer coupled between the articulable assembly and the first point on the body and capable of generating a signal representative of a change in length between the first point and the second point on the body when the body is moved.

BRIEF DESCRIPTION OF THE DRAWINGS

For a more complete understanding of the present invention, reference is made to the following detailed description of an exemplary embodiment considered in conjunction with the accompanying drawings, in which.

DETAILED DESCRIPTION OF THE EXEMPLARY EMBODIMENT

Figure 1:
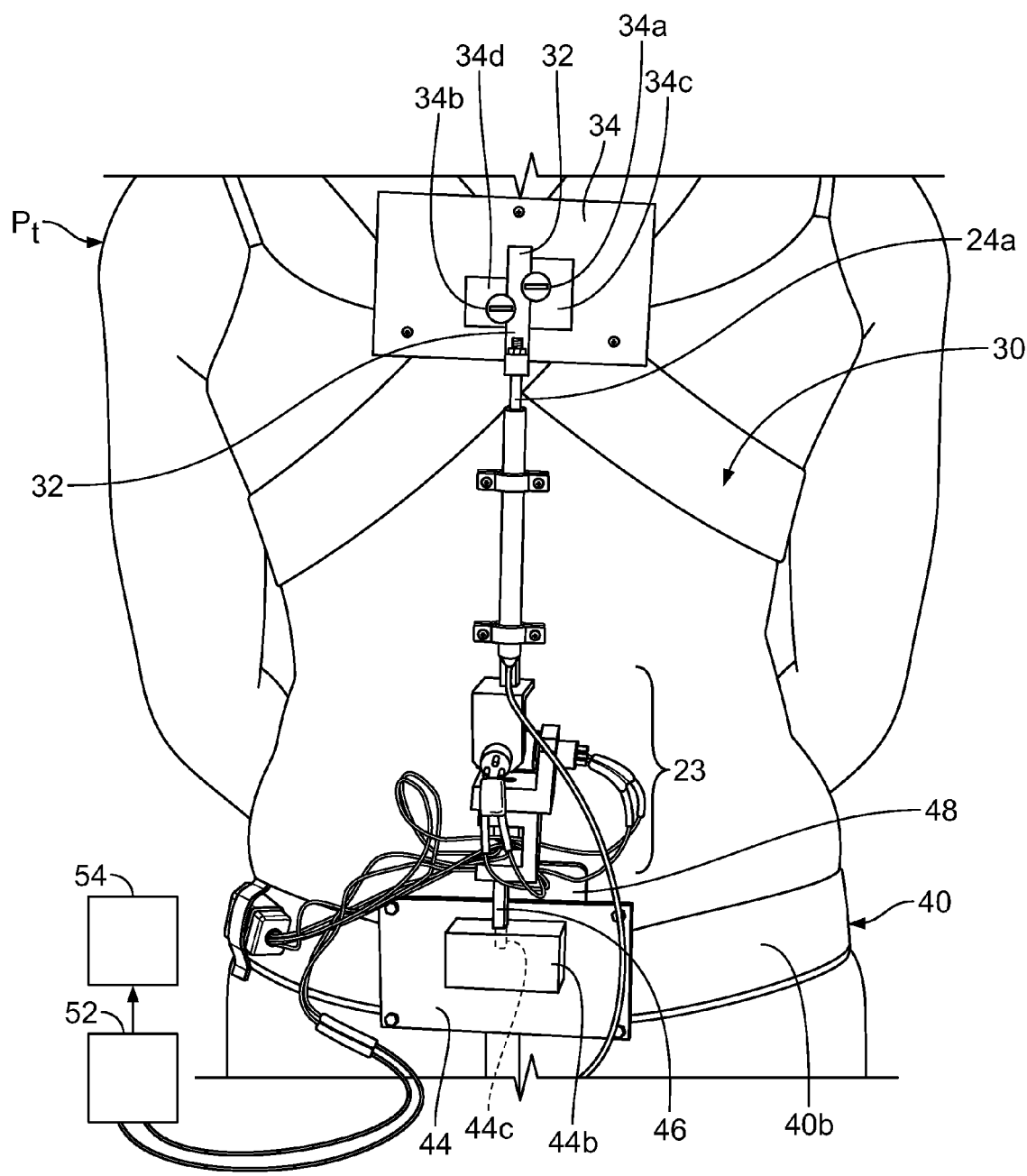
FIG. 1 is a perspective view of a goniometer system in accordance with an embodiment of the present disclosure worn by a person.
Figure 2:
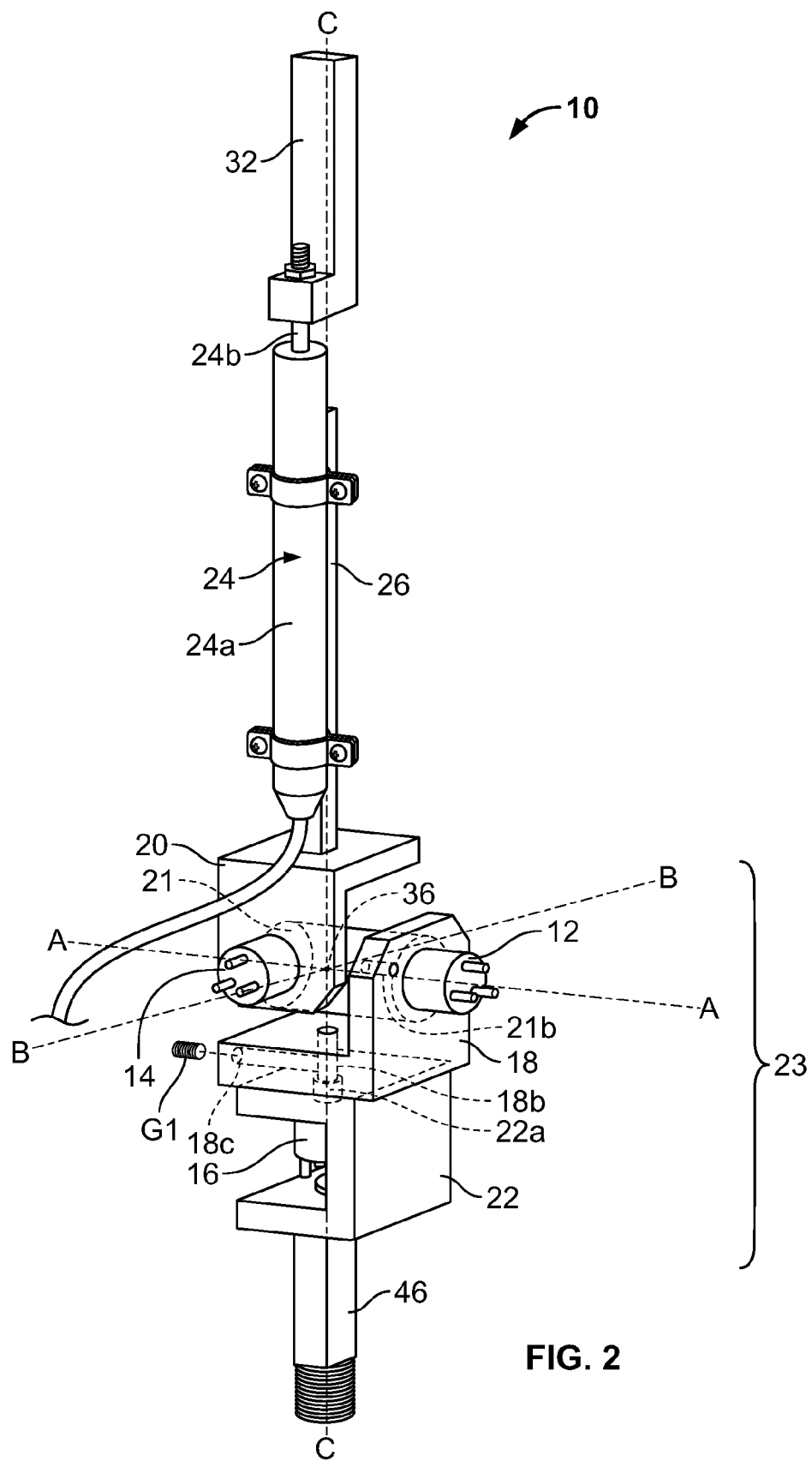
FIG. 2 is a perspective view of the goniometer of FIG. 1.

FIGS. 1 and 2 illustrate a spinal goniometer system 5 with a goniometer 10 constructed in accordance with an exemplary embodiment of the present invention. The goniometer 10 has potentiometers 12, 14, 16, which are commercially available, for example, Vishay/Spectrol potentiometers from Vishay, Inc of Shelton, Conn. and which are described in greater detail herein below. The Potentiometers 12, 14, 16 may be used to measure rotary motion along three axes. More particularly, potentiometer 12 measures the flexion and extension of the spine about axis A-A, potentiometer 14 measures lateral bending about the axis B-B, and potentiometer 16 measures rotation of the spine about axis C-C.

Axes A-A, B-B, and C-C intersect at an intersection-point 36. This arrangement enables rotation of the potentiometers 12, 14, 16 on the respective axes A-A, B-B-, or C-C independently, without inducing mechanical cross-talk (i.e., un-applied rotational motion of the other potentiometers) on the other axes. In addition, the potentiometers may be independently, simultaneously rotated if induced to do so by movement of the spine. The absence of mechanical and electrical cross talk between the potentiometers and the mechanical movement of the goniometer 10 is described in greater detail below.

Figure 5:
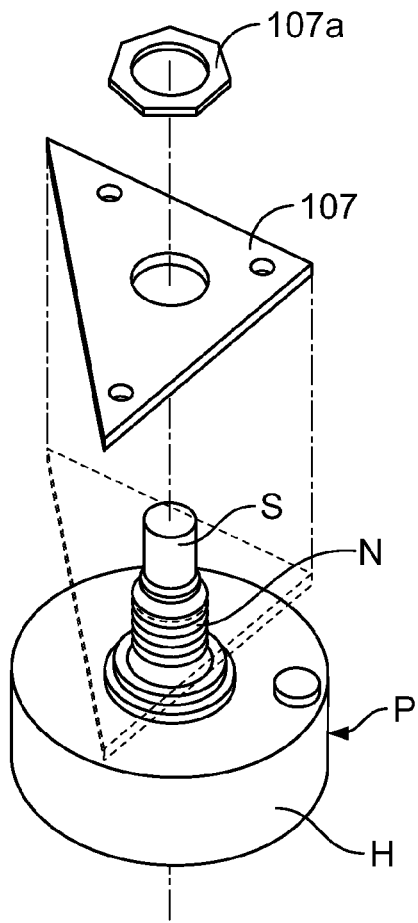
FIG. 5 is an exploded view of a potentiometer assembly.

The potentiometers 12, 14 and 16 are mounted in three flanges 18, 20, 22, respectively, and are used to attach the flanges together into an articulable assembly 23. The flanges 18, 20, 22 have threaded holes that are adapted to accept the threaded nipples of the potentiometers 18, 20, 22, respectively. Referring to FIG. 5, rotatable potentiometers P are known and are commercially available. As shown, some known potentiometers have a housing H containing a resistive element (not shown) to which an electrical potential may be applied and a central stem S rotatable relative to the housing H and coupled to a conductive wiper (not shown) for conducting electricity though the wiper to a point of contact with the resistive element, thereby varying the distance electricity must pass through the resistive element and varying the resultant overall resistance. In an embodiment, the potentiometers 12, 14, 16 have a 10K Ohm output and a single turn limitation (the shaft can only turn 360° and at that point it gives a maximum output of 10K ohm). Potentiometers having other resistance ranges can be readily used given comparable adjustments to the other circuit elements of the circuitry described below. The potentiometer is a panel-mount type with solder turret terminals. An exemplary potentiometer has a housing H diameter of 12.77 mm and length of 7.75 mm. The shaft S has a length of 12.78 mm and a diameter of 3.17 mm. Other sized potentiometers may also be utilized in alternate embodiments of the present disclosure. In an embodiment of the present disclosure, the potentiometers 12, 14, 16 may serve both as a mechanical pivot and as a transducer for indicating angle of pivot via variation in electrical resistivity, i.e., based upon the angular displacement of the stem S/wiper relative to the housing H/resistive element. The housing H may be provided with a threaded nipple N for mounting purposes. The potentiometer P shown in FIG. 5 is accompanied by a mounting plate 105, by which it may be attached to a flange similar to flanges 18, 20, 22, as described below in reference to FIGS. 5 and 16. The potentiometers 12, 14, 16 may be attached to the flanges 18, 20, 22 by a variety of approaches, such as bushing mount or servo mount, e.g., using a plurality of screws that screw into a flange around the mounted potentiometer, a servo mount using mounting cleats or screws that screw into threaded apertures in the potentiometer, or other known arrangements.

FIGS. 1 and 2, however, show an embodiment of the goniometer 10 wherein the threaded nipple portions N of the potentiometers 12, 14, 16 housings H are screwed into threaded apertures, e.g., 22a, in the respective flanges 18, 20, 22. More particularly, potentiometer 16 is threaded through threaded potentiometer aperture 22a (depicted in dotted lines) in U-shaped flange 22 with the stem S (see FIG. 5) extending up into a mating stem aperture 18b of the middle, L-shaped flange 18. A grub (set) screw G1 threads into a mating threaded screw aperture 18c to retain the stem S of potentiometer 16 within aperture 18b in flange 18. The potentiometer 16 may be tightened in aperture 22a to a degree that prevents movement of the potentiometer housing H relative to flange 22 when the goniometer 10 is used. A thread sealant, spring washer or lock nut may be used to lock the potentiometer housing H/nipple N in a given position relative to flange 22. The stem S of potentiometer 16 may then be rotated to a given start position relative to the housing H of the potentiometer 16. The flange 18 may also be rotated to a given start position relative to the stem S of potentiometer 16 and the housing H of potentiometer 16 before the grub screw G1 is tightened, locking these elements into a given relative orientation. This results in an articulable mechanical linkage between flanges 22 and 18 intermediated by potentiometer 16, whereby the housing of potentiometer 16 is secured to the flange 22 and the flange 18 is pivotally connected to flange 22 via the rotable stem S of potentiometer 16. The angle of rotation of flange 18 relative to flange 22 on axis C-C can therefore be electrically interpreted by the potentiometer, viz., by the observable electrical effect (change of resistance) resulting from changing the position of the stem relative to the housing (and the associated internal wiper and resistive element). The resistance through the potentiometer 16 may be measured and converted to resistance/voltage data, which varies as the stem S is turned and can be correlated to a given angular orientation or degree of turning of the stem S.

Figure 16:
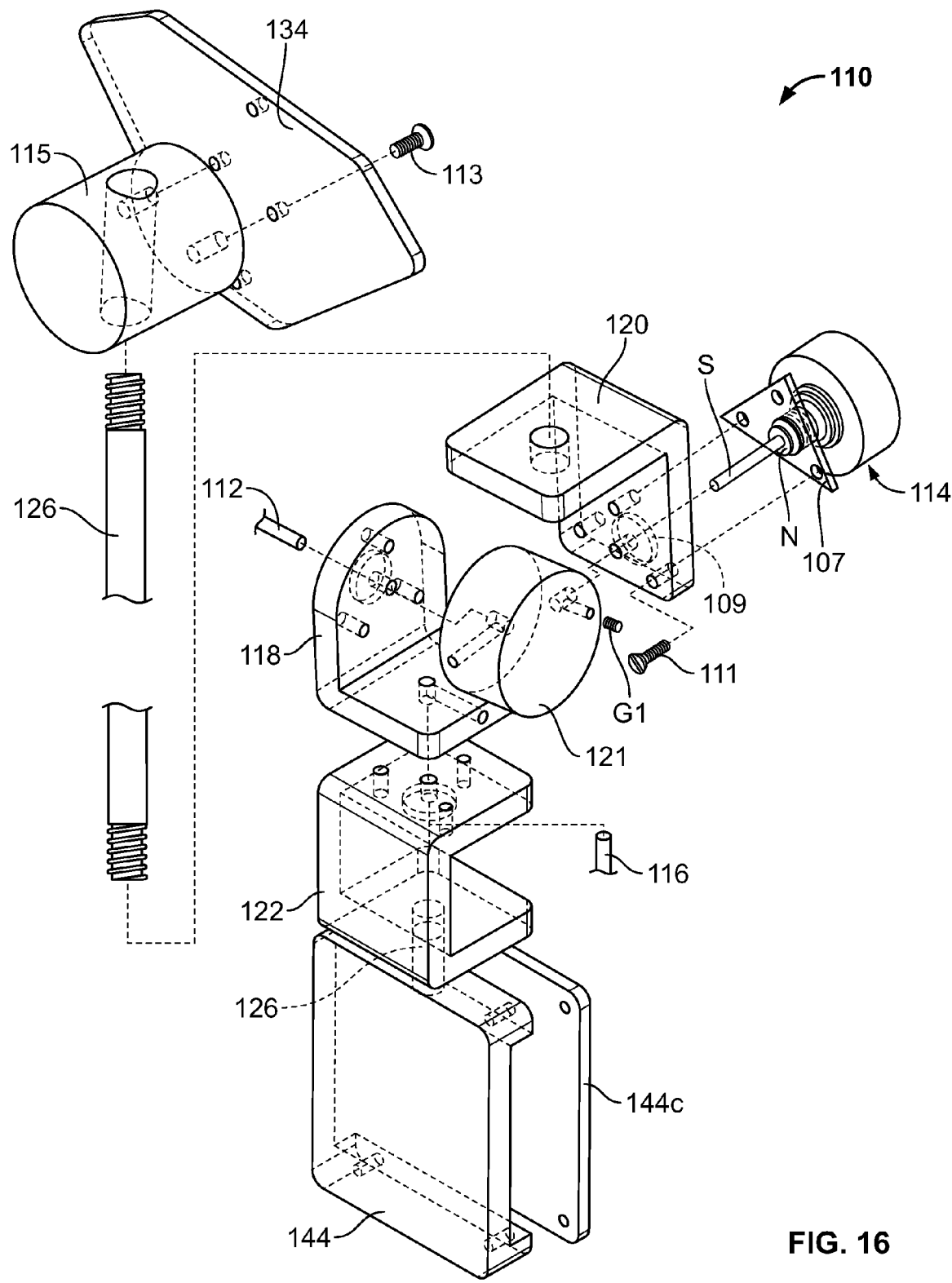
FIG. 16 is an exploded, perspective view of a goniometer in accordance with an embodiment of the present disclosure.

This same basic relationship may be used to attach, articulate and measure the angle of articulation of flange 20 relative to flange 18 on axes A-A and B-B, but with the intermediation of an additional mechanical link, i.e., cylinder 21 (shown in dotted lines in FIG. 2). More particularly, after the nipple N of potentiometer 12 is threaded into an aperture in flange 18, the stem S of potentiometer 12 is inserted into a mating aperture 21b in an end of coupler cylinder 21, where it is gripped by a grub screw threaded into coupler cylinder 21 at right angles to the mating stem aperture 21b in like manner as grub screw G1 grips the stem S of potentiometer 16 in stem aperture 18b. In a similar fashion, after the nipple N of potentiometer 14 is threaded into aperture 20a of flange 20, the stem S of potentiometer 14 is inserted into a mating stem aperture in the side of cylinder 21 and is held there with a grub screw. A similar arrangement is depicted in FIG. 16, to be described below. The stem apertures, e.g., 21b may be non-cylindrical to mate with a potentiometer stem that is non-cylindrical, e.g., both may have hexagonal shapes or be cylindrical with a flat side. The stems may be retained in the stem apertures, e.g., 21b, by means other than a grub screw, e.g., by resiliently urged detent mechanisms, by adhesives or circlips.

The stem apertures, e.g., 21b, in the coupler cylinder 21 are at right angles relative to one another, such that the axes of rotation of the potentiometers 12, 14 are at right angles and converge at the tri-axial intersection point 36. As noted above, the axis of rotation C-C of potentiometer 16 also intersects intersection point 36. The coupler cylinder 21 could be replaced with a coupler of any shape, such as a cube or an L-shaped solid, so long as it supports and retains the stems of the potentiometers 12 and 14 in apertures at right angles to one another and does not interfere with the rotation of the flange 20 on axes A-A and B-B.

When threading the potentiometers 12, 14, 16 in their corresponding threaded apertures, e.g., 22a in the respective flanges 18, 20, 22 and/or when coupling the stems S of the potentiometers 12,14,16 to the coupler cylinder 21 or the flange 18 into which it inserts, it may be desirable to position the stem relative to the potentiometer housing H (wiper relative to the resistive element) at a position allowing the potentiometer 12, 14, 16 to register over the anticipated range of motion of the flange 18, 20, 22 to which is it attached (when moved by the patient). For example, if the stem S has a 180 degree range of rotation and the flange 18, 20, 22 to which it is coupled is anticipated to have a 45 degree range of rotation (+/−22.5 degrees to either side of a central start position), the stem S should be positioned at an angular position that allows the stem to be rotated through the anticipated 45 degree range. This may be done by observing the position visually or noting the electrical resistance through the potentiometer 12, 14, 16, which is indicative of the angle of the wiper when the stem of the potentiometer is coupled to the attached element. In the instance where a grub screw, e.g., G1 is intended to bear upon a flat on the stem, which requires a specific angular orientation of the stem relative to the respective coupler or flange, the range of the potentiometer may be set by selected tightening of the housing H in the threaded potentiometer aperture, e.g., 22a, that receives it or by the use of washers and/or a lock nut that establish a tight condition associated with a given degree of angular rotation of the housing H in the threaded hole 22a. An alternative arrangement for mounting potentiometers 12, 14, 16 is described below.

The goniometer 10 may optionally include a linear displacement sensor/transducer 24, such as a Honeywell MLT Series Linear Position Transducer from Honeywell of Morristown, N.J., which may be used to measure a change in length of the transducer 24 due to arching of the spine of the patient. The transducer 24 has a first portion 24a that is mounted on a top rod 26 extending from the upper L-shaped flange 20, e.g., by holders 28 clamped around the transducer 24 and held together by fasteners, such as nuts and bolts or rivets (not shown). The holders 28 may be fastened to the top rod 26 by screws, rivets, glue or other fasteners (not shown), or may encompass and clamp the top rod 26 against the transducer 24. A thin sheet of rubber or double sided tape may be placed between the transducer 24 and the holders 28 to aid the holders 28 in gripping the transducer 24.

Figure 6:
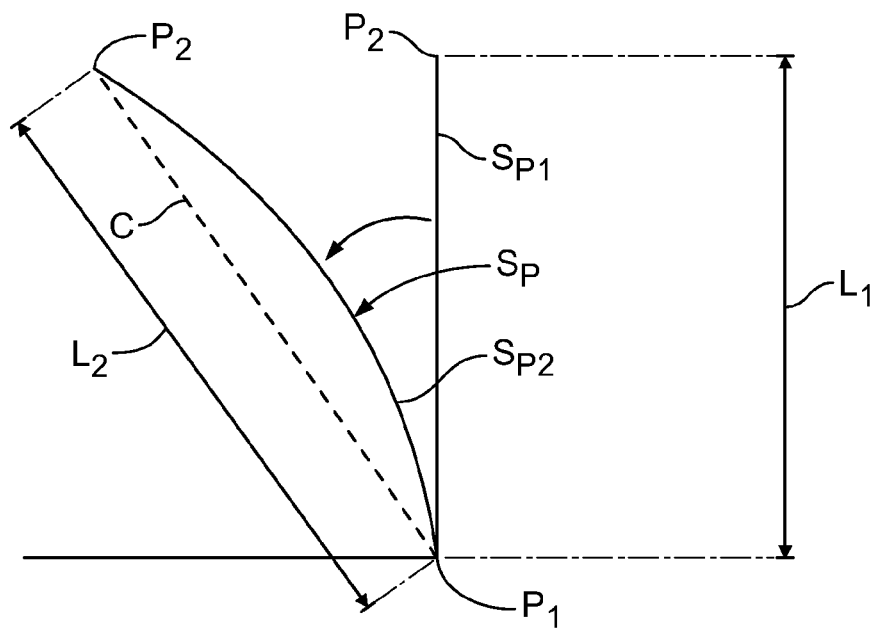
FIG. 6 is a schematic depiction of a spine in two positions.

A second portion 24b of the transducer 24 is coaxially, linearly moveable relative to the cylindrical first portion 24a. As shown in FIG. 6, a spine Sp may curve as it moves from an upright position Sp1, having a length L1 between two given points P1 and P2 on the spine Sp, to a forward, curved position Sp2. The chordal length C between P1 and P2 in spinal position Sp2 has a length L2 which may differ from L1. The transducer 24 may be utilized to measure both L1 and L2 and any distance between P1 and P2 at any given intermediate position in the range of motion of the spine. As noted, the angular position of the spine Sp can be measured by potentiometer 12. Changes in the arc length of the spine during its transition from a straighter to a more arcuate confirmation associated with natural spinal alignment or forward bending, which implies a relative compression of the anterior side of the spine and an expansion of the posterior side, may be measured with the transducer 24. As with any/all the measurements taken by the goniometer 10, the measurements conducted by the transducer 24 may be sampled continuously at a selected sampling rate and recorded for playback and analysis, as shall be described below. Any or all of the measurements taken of motion by the goniometer 10 may be sampled simultaneously with other measurements, giving a coordinated, cross-related view of simultaneous motions. The transducer 24 exhibits a change in resistance proportional to the linear displacement of the first portion 24a to the second portion 24b.

Figure 3:
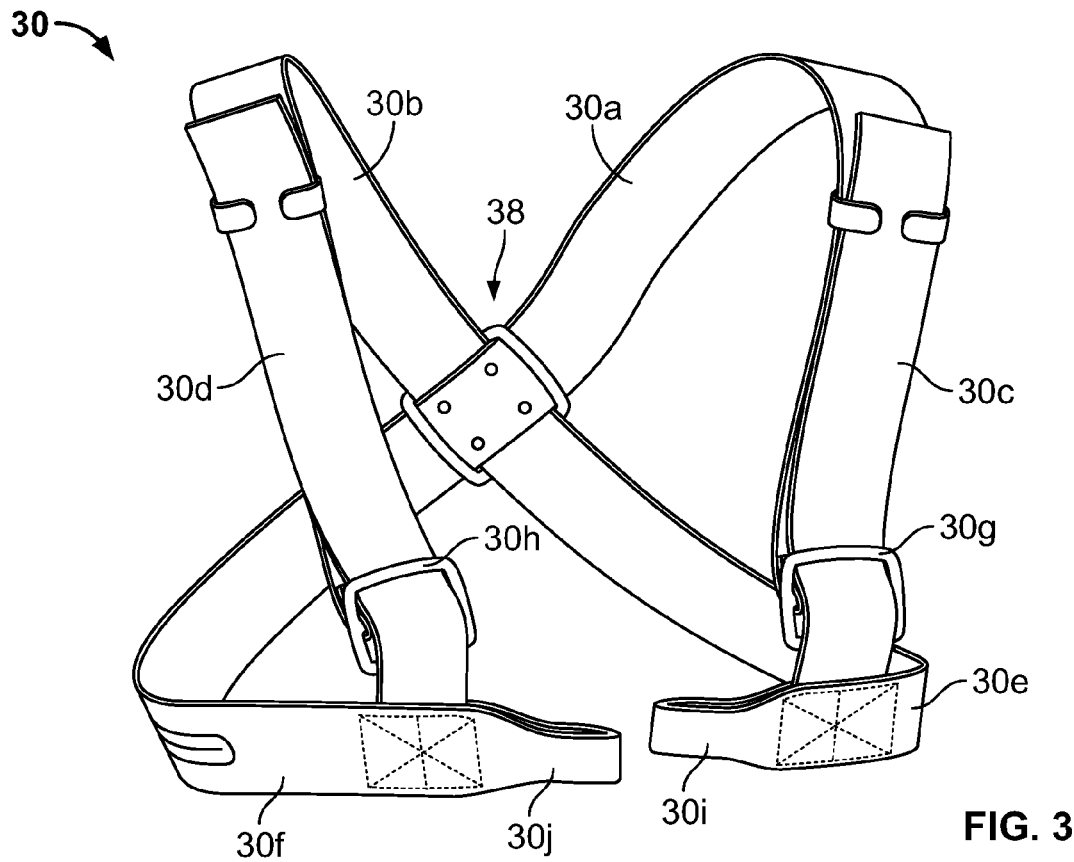
FIG. 3 is a perspective view of a top harness of the goniometer of FIG. 1.
Figure 4:
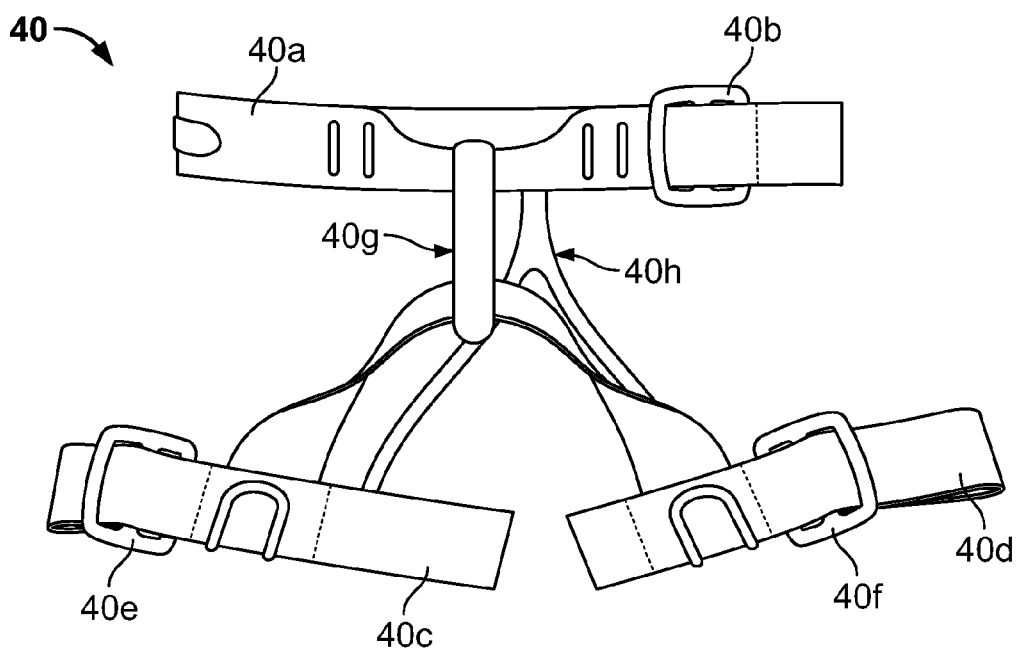
FIG. 4 is a perspective view of a bottom harness of the goniometer of FIG. 1.

Referring to FIGS. 1, 3 and 4, the goniometer 10 may be coupled to a harness or harnesses to allow it to be worn by a patient Pt during range of motion testing. A top harness 30 may be attached to the upper portion 24a of the transducer 24, e.g., via bracket 32, which is clamped to plate 34 via screws 34a, 34b and clamp blocks 34c, 34d. The bracket 32 may be L-shaped to compensate for the lateral displacement of the transducer 24 relative to the top rod 26, e.g., to bring the point of attachment of the bracket 32 to the plate 34 into line with the axis of the top and bottom rods 26, 46.

The plate 34 may be attached to the top harness 30 at an intersection 38 of crossing back strap portions 30a, 30b via rivets, screws, bolts and nuts, gluing, overmolding or other commonly known expedients. The back strap portions 30a, 30b extend over the shoulders to front strap portions 30c, 30d that attach to belt portions 30e, 30f that extend from the intersection 38 via buckles 30g, 30h. The belt portions 30e, 30f terminate in loops 30i, 30j that may be coupled together by a carbineer clip, by Velcro or in a conventional belt and buckle arrangement (not shown). In an embodiment of the present disclosure, the top harness 30 is adjustable to fit snugly on a variety of patients, e.g., via the buckles 30g, 30h and the adjustable conjunction of end loops 30j, 30i.

A bottom harness 40 may be in the form of a climbing harness and is attached to the bottom portion of the goniometer 10 via an attachment plate 44. The bottom harness 40 has an adjustable belt portion 40a in the form of a loop closed by buckle 40b and a pair of leg loops 40c and 40d, which may also utilize buckle closures 40e, 40f to allow them to be adjusted to different patients. The leg loops 40c and 40d are coupled to the belt portion 40a via front and rear webs 40g, 40h, which attach to the belt portion at the front and rear thereof, respectively, and then bifurcate to couple to the leg loops 40c, 40d. The non-adjustable attachment of different portions of the harnesses 30, 40, e.g., conjoining 30d to 30f and 40g to 40c, may be made by stitching, glue, Velcro, rivets or other conventional means, e.g., 40g may have a loop construction allowing belt 40a to be threaded there through. The attachment plate 44 may be riveted or bolted to the bottom harness 40, e.g., to belt portion 40a. Alternatively, the attachment plate 44 may be utilized with a backer plate like that shown in FIG. 16 to clamp the belt portion 40b there between by fasteners such as nuts and bolts or rivets conjoining the attachment plate 44 to a backer plate like backer plate 140c of FIG. 16. The attachment plate 44 has a rod block 44b with an aperture 44c therein for receiving an end of a bottom rod 46. The aperture 44c and the bottom rod 46 may be threaded to allow a threaded coupling thereof. The other end of the bottom rod 46 couples to the U-shaped, bottom flange 22, e.g., via threaded attachment to mating aperture and may be locked in place with a lock nut. Alternatively, the bottom rod 46 may be attached to the rod block 44b and/or the bottom flange 22 by welding or gluing or may be monolithically molded therewith. The same alternatives are applicable to the top rod 26 and its coupled relationship to the upper L-shaped flange 20. In the case of removable top and bottom rods 26, 46, rods of different length may be provided with the goniometer 10, e.g., in a set, to accommodate the various dimensions of patients (tall/short, etc.) and for different applications of the goniometer, e.g., to measure different portions of the spine and/or to measure other joints. While two harnesses 30 and 40 are shown, they could, in alternative embodiments, be coupled into a single harness, or divided into more than two conjoinable parts.

The belt portion 40a, may, .e.g., be adjustable over a range for waists/hips sizes, e.g., 20" to 50" and other sized belt portions 40a may be used to accommodate smaller or larger dimensions. FIG. 1 shows the bottom harness 40 fitted around a patient's hips. The goniometer 10 can be moved up and down on the patient's torso, e.g., to the waist, to allow the goniometer 10 to be positioned proximate the section of the spine that is of interest, e.g., to measure conformation or motion thereof. For example, the physician may be interested in determining the range of motion of the spine between two specific vertebrae, e.g. L2 and T5. Depending on the patient's anatomy, a wedge 48 may be inserted between the attachment plate 44/bottom harness 40 and the patient's anatomy, when needed to orient the goniometer 10 approximately in an aligned orientation with the bottom rod 46 and top rod 26 vertically aligned and/or to avoid possible Gimbal lock when the patient moves. The wedge 48 may be made from hard materials such as wood or plastic or may be formed from a dense foam which may be more comfortable to the patient, depending upon where it is required to be positioned. A variety of wedges 48, of different angular displacements e.g., 10, 20 or 30 degrees, may be provided to adjust the position of the goniometer 10 to a variety of patients and/or to a variety of positions of the goniometer 10 relative to the patient's body.

While the present disclosure shows the application of the goniometer 10 to the spine in the lower back region, it may also be useful in measuring and analyzing the motion of the cervical spine and other joints of the human anatomy, e.g., the elbows, knees, shoulders, etc. While the present disclosure refers to use of the goniometer on humans, it may also be used to assess the functionality and condition of the spines and joints of animals, such as working animals like race horses, companion animals like dogs and cats, wild animals, marine animals, and any other animal that may need assessment, analysis, treatment or academic study.

When putting on the goniometer 10, the patient may step into the bottom harness 40 first, adjust the belt 40a to their waist/hip size, then put his/her arms through the top harness 30 and adjust it to his/her chest size. The examining physician or technician can then adjust the fit and initial position of the goniometer 10. The goniometer 10 may be used with the patient fully clothed or clothing may be removed to allow positioning of the goniometer 10 relative to the patient's anatomy, e.g., extending between specific vertebrae. The potentiometers 12, 14, 16 of the goniometer 10 are responsive to minimal torque and rotate (or extend—in the case of the transducer 24) in response to patient motion when the goniometer 10 is secured to the patient.

Figure 17:
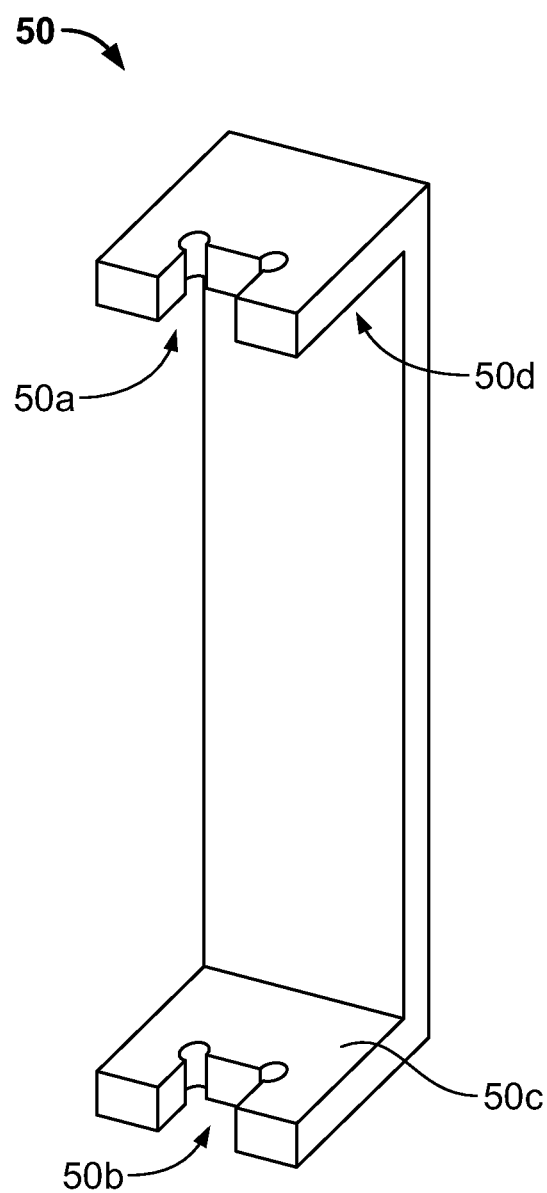
FIG. 17 is a perspective view of a tool for placing a goniometer in a reference position in accordance with an embodiment of the present disclosure.

Prior to positioning the goniometer on the patient, the goniometer may be placed into a reference position to observe and record the potentiometer 12, 14, 16 and/or transducer 24 readings in that reference position. For example, the goniometer 10 may be suspended by the bracket 32 in a pendulous, plumb position and the potentiometer readings/angles read. Alternatively, the goniometer 10 may be positioned on or against a reference gauge or tool that abuts against one or more surfaces known to hold one or more of the goniometer 10 components in a given orientation. For example, the goniometer 10 may be placed upon a flat surface and/or abutted against a straight edge or placed in a U or V-shaped gauge that holds the flanges 12, 14, 16 at a predetermined orientation. A C-shaped gauge 50 (see FIG. 17) may be utilized to position or maintain the goniometer 10 in a reference position. The C-shaped gauge 50 has top and bottom recesses 50a, 50b that may matingly embrace the cross-sectional shape of the top and bottom rods 26, 46, such that they are assured to be in a given relative orientation when fully engaged with the C-shaped gauge 50. As shown, the recesses 50a, 50b would mate with a rod 26, 46 having a square cross section. Other shaped rods 26, 46 would be embraced by complementarily shaped recesses 50a, 50b. The C-shaped gauge 50 may be sized and positioned so that it contacts the top and bottom rods 26, 46 of the goniometer 10 and may also be dimensioned to provide other reference surfaces that portions of the goniometer may abut against to establish a reference position. For example, the surface 50c may abut against the lower, U-shaped flange 22 and the surface 50d may abut against the upper L-shaped flange 20. The C-shaped gauge 50 may be used to straighten out the goniometer 10, rotating each of the potentiometers 12, 14, 16 to a reference position having a given associated resistance. The gauge 50 or another type of gauge may be used at any given time, e.g., after the goniometer 10 is worn by the patient and assuming a given posture, or prior to being worn.

The output data from the respective potentiometers 12, 14, 16 and the transducer 24 may be recorded to reflect a given reference position and later used to calibrate/interpret output data from the goniometer 10 when it is worn by the patient. When the goniometer 10 is applied to a patient, initial data readings taken at a given initial patient position, e.g., standing up straight, may be compared to readings relative to the un-worn/un-installed reference position and the changes noted. In this respect, the goniometer 10 may express position data in terms of change data (relative to an initial position), rather than absolute data. Initial change data attributable to the act of putting the goniometer 10 on may be useful for indicating information about the posture or conformation of the patient's anatomy when in a given position, e.g., standing upright and motionless. After being coupled to the patient, the orientation of the goniometer 10 may be adjusted, e.g., by a wedge 48. The position data obtained from the goniometer can be recorded at all stages from a reference, uninstalled position to being first installed in a given posture, then as changed by a wedge 48, followed by data resulting from the patient's subsequent movement. The wedge 48 may be used to permit the goniometer 10 to follow a given range of patient movement without experiencing gimbal lock.

Figure 7:
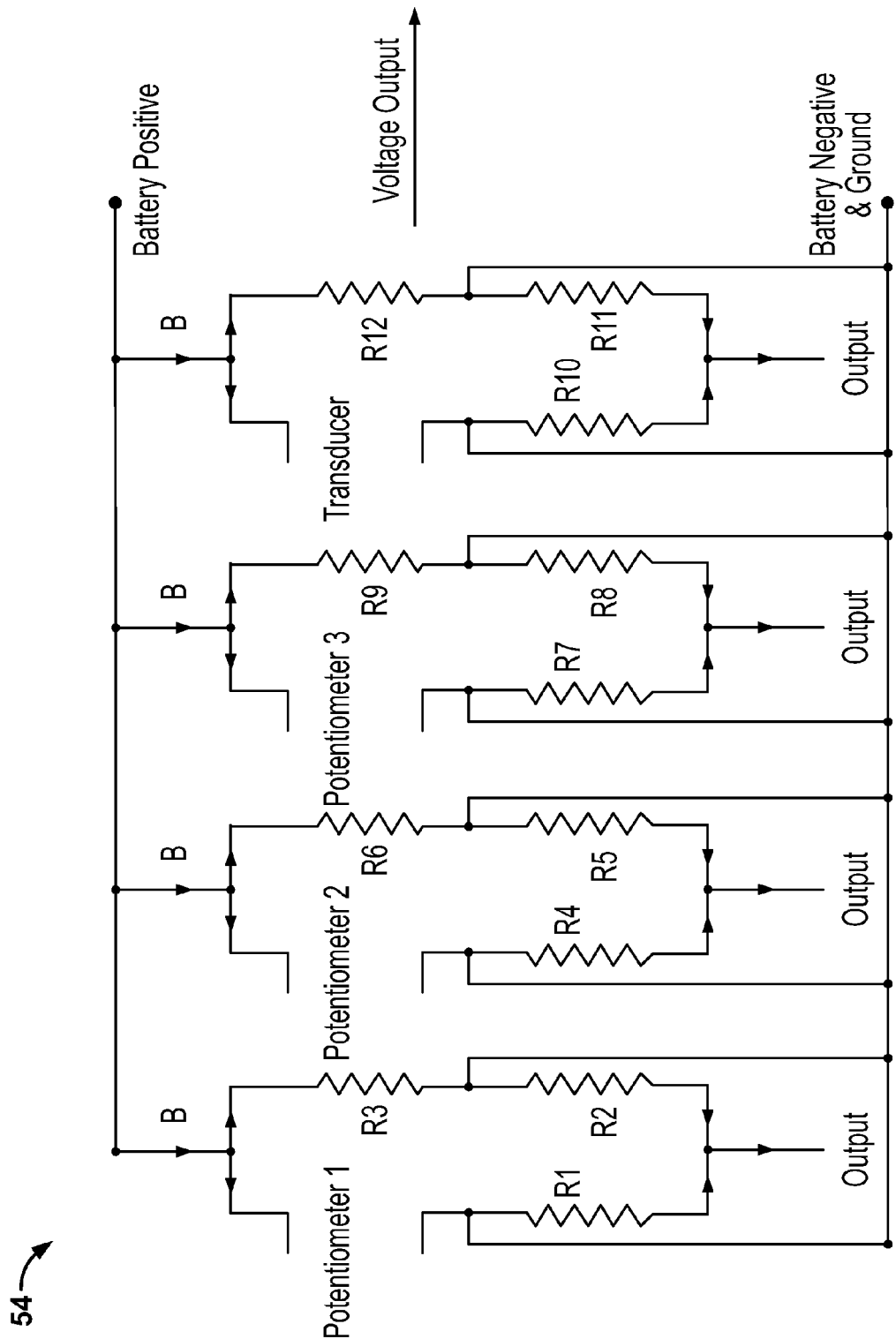
FIG. 7 is a schematic depiction of a circuit in accordance with an embodiment of the present disclosure.
Figure 8:
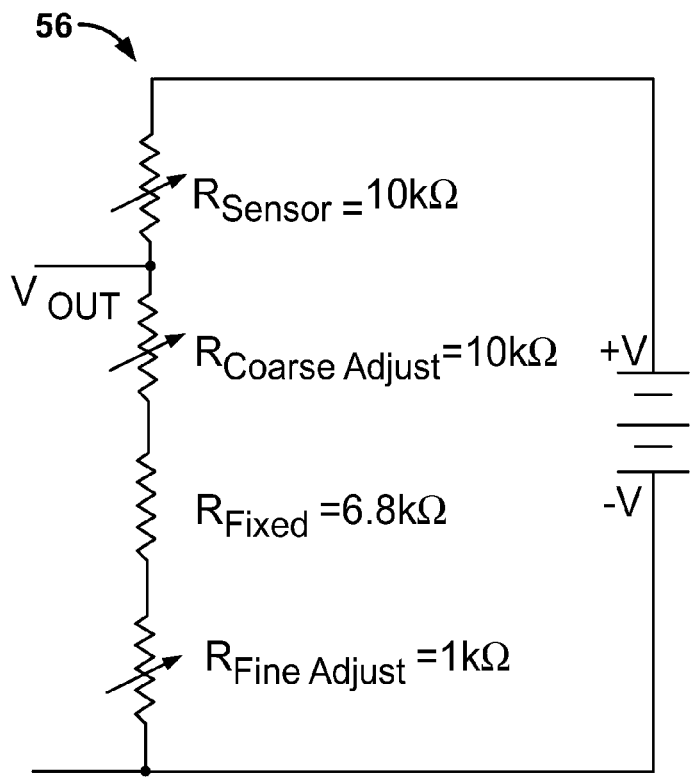
FIG. 8 is a schematic of a circuit in accordance with another embodiment of the present disclosure.

The potentiometers 12, 14, 16 and the transducer 24 are electrically connected to an interpreter 52 which monitors the change in electrical properties, e.g., the changes in resistance at various mechanical position states of the goniometer 10, converts those changes in electrical properties to digital data and passes the digital data to a computer 54 for recording and analysis. In one embodiment, the interpreter 52 utilizes Wheatstone bridges 54 as shown in FIG. 7. Each of the three potentiometers 12, 14, 16 and the transducer 24 (see FIG. 2) is connected to the terminals of a one of four Wheatstone bridges powered in parallel by a voltage, in the instance shown, supplied by, e.g., a battery. Any other voltage source, such as a power supply, could be used. As is known, a Wheatstone bridge is an electrical circuit that may be used to measure a resistor value by comparing it to known resistances in the circuit, e.g., R1-R3 for the Wheatstone bridge connected to potentiometer 1. If the bridge is balanced (R1=R2 and Potentiometer 1=R3), then the voltage at the output will be zero. If the bridge is unbalanced, a voltage is present at the output proportional to the resistance value of the unknown resistor. FIG. 8 shows a circuit 56 utilizing an alternative approach, wherein the resistance of a potentiometer 12, 14, 16 (represented by $R_{sensor}$=10K ohms) is placed in series across a battery voltage with three other resistors, two of which are variable $R_{coarse\ Adjust}$ and $R_{Fine\ Adjust}$ and a fixed resistor— $R_{Fixed}$. The potentiometer 12, 14, 16 to be read can then be positioned at the angle associated with maximum resistance, e.g., 10K ohms, and the variable resistors adjusted until the output voltage $V_{Out}$ is one half of the battery voltage (at which point the total resistance of the three balancing resistors will equal 10 ohms). When the potentiometer 12, 14, 16 under test is set at the angle resulting in 0 ohms, $V_{Out}$ will be equal to the battery voltage. In this manner, the position of the potentiometer 12, 14, 16 can be indicated by the voltage $V_{Out}$. Each potentiometer 12, 14, 16 would be connected to a circuit 56 and would generate an associated output voltage $V_{Out}$.

The interpreter 52 may also include an instrument to receive the voltage output from the potentiometers 12, 14, 16 and the transducer 24 and convert that output to digital data. The analog voltage output from circuits 54 or 56 may be received by a commercially available data acquisition instrument, such as a DATAQ data acquisition instrument available from Dataq Instruments, Inc. of Akron, Ohio. This is an example of many such units that are commercially available. One model of DATAQ data acquisition instrument is a portable data recording module with 8 single-ended analog inputs and may be used to obtain and display potentiometer outputs. The voltage output is measured by this device, converted to digital form and shared with a computer 58. The DATAQ hardware works in conjunction with WINDAQ7, also commercially available from Dataq, Inc., which may be loaded into the computer 58. The goniometer 10 may be connected to the interpreter 52 through a cable, such as a twisted ribbon cable 60 of a length sufficient to allow the patient to walk about and perform the range of motion tests. The WINDAQ Data acquisition software allows users to record and analyze waveform data recorded by the data acquisition instrument. WINDAQ simultaneously supplies a real-time graphical display of as many channels as needed for showing the potentiometer voltage levels. Each channel can be labeled, played back, and analyzed with the built-in analysis functions. The software will display the voltage output from the potentiometers proportional to each angle turned and proportional to the linear displacement of the transducer.

Figure 9:
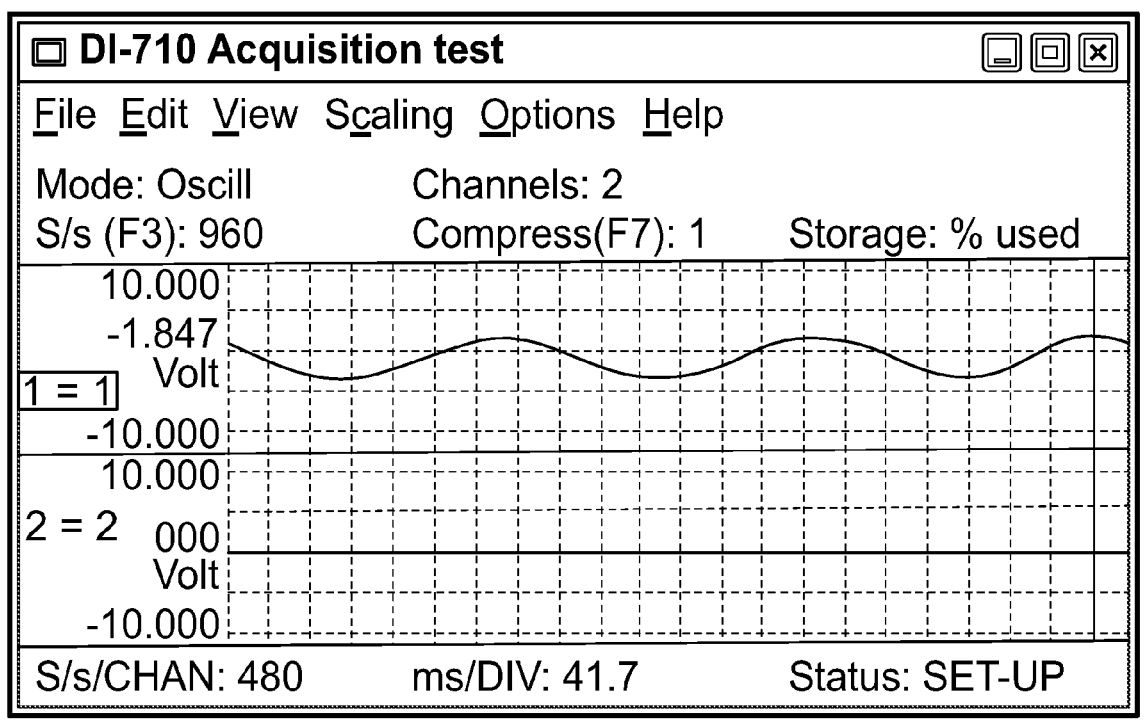
FIG. 9 is a screen shot of output of data acquisition software.

FIG. 9 shows an example of the data that is displayed by the WINDAQ software. As the potentiometers 12, 14, 16 are turned and the linear displacement of the transducer 24 occurs, the amplitude of the wave displayed changes. When the spinal goniometer 10 is tested, there is one wave displayed for each of the potentiometers 12, 14, 16 and one for the transducer 24. The wave values may be shared with other computer programs running on the computer 58 or another computer, such as animation programs which convert the potentiometer angles to animations of a model of a spine or other jointed limb and recorded for re-projection and analysis.

In accordance with one procedure for using the goniometer system 5, the goniometer 10 is connected to the interpreter 52, which is connected to the computer 58. The goniometer 10 is optionally positioned in a reference position and the potentiometer 12, 14, 16 angles and transducer 24 position is observed. The goniometer 10 is then secured to the patient using the harnesses 30, 40. Optionally, the patient assumes a reference position, such as standing straight, and the data from the goniometer system 5 is observed and recorded. Optionally, a reference gauge like C-shaped gauge 50 is employed on the goniometer as it is worn by the patient to establish a second reference position, and the data associated with the second reference position is observed and recorded. The gauge is then removed, allowing the goniometer 10 to assume positions determined by the patient's anatomy, posture and movement state. If the data associated with the first or second reference position or physical inspection indicates that the patient requires a wedge 48 to be inserted to reposition the goniometer relative to the patient, then a wedge 48 of a first angle is inserted and the effect of the wedge 48 on the position data is observed. If necessary, additional or substitute wedges 48 with different angles are inserted in order to position the goniometer 10 in a suitable start position and insure that gimbal lock is avoided. The patient then executes assigned movements, resulting in the continuous and simultaneous generation and recordal of angle and extension data as captured by the goniometer system 5.

Experimental Results

Prior to use, each potentiometer 12, 14, 16 was calibrated so as to permit direct measurement of the respective angles from the output. The sensors in the device were connected to a single circuit board with multiple Wheatstone bridge circuits. Upon rotation of the rotary potentiometer shafts, an electrical signal was generated in each respective bridge due to the unbalancing of the circuit. The alignment of the sensors reduces the need for complex computations to arrive at flexion/extension, rotation and lateral bending of the spine. The following data was obtained and the Average and Standard Deviation was calculated as shown in Table 1 for a first potentiometer, 12.

TABLE 1

Potentiometer #1 Voltage Output Results

| Angle Degrees | Voltage Output (Volts) | | | Average | Standard Deviation |
| --- | --- | --- | --- | --- | --- |
|  | #1 | #2 | #3 |  |  |
| −50.000 | 0.529 | −0.529 | −0.529 | −0.529 | 0.000 |
| −40.000 | −0.431 | −0.430 | −0.430 | −0.430 | 0.001 |
| −30.000 | −0.334 | −0.339 | −0.341 | −0.338 | 0.004 |
| −20.000 | −0.225 | −0.226 | −0.226 | −0.226 | 0.001 |

TABLE 1-continued

Potentiometer #1 Voltage Output Results

| Angle Degrees | Voltage Output (Volts) | | | Average | Standard Deviation |
|---|---|---|---|---|---|
| | #1 | #2 | #3 | | |
| −10.000 | −0.109 | −0.112 | −0.114 | −0.112 | 0.003 |
| 0.000 | 0.003 | −0.004 | −0.002 | −0.001 | 0.004 |
| 10.000 | 0.112 | 0.118 | 0.112 | 0.114 | 0.003 |
| 20.000 | 0.256 | 0.258 | 0.256 | 0.257 | 0.001 |
| 30.000 | 0.400 | 0.400 | 0.400 | 0.400 | 0.000 |
| 40.000 | 0.552 | 0.552 | 0.554 | 0.553 | 0.001 |
| 50.000 | 0.729 | 0.721 | 0.720 | 0.723 | 0.005 |

The same type of testing (repeated three times) was conducted on the remaining potentiometers 14, 16 and the transducer 24, with the following results:

TABLE 2

Potentiometer #1 Voltage Output Results Comparing Sensors

| Angle/Linear Displacement | Voltage Output (Volts) | | | | | | | | | Average Sensor 2 | Average Sensor 3 | Average Transducer |
|---|---|---|---|---|---|---|---|---|---|---|---|---|
| | Sensor 2 | | | Sensor 3 | | | Transducer | | | | | |
| | #1 | #2 | #3 | #1 | #2 | #3 | #1 | #2 | #3 | | | |
| −50.000 | 0.000 | 0.001 | 0.001 | 0.001 | 0.002 | 0.002 | 0.826 | 0.825 | 0.823 | 0.001 | 0.002 | 0.825 |
| −40.000 | 0.000 | 0.000 | 0.001 | 0.002 | 0.002 | 0.002 | 0.823 | 0.823 | 0.825 | 0.000 | 0.002 | 0.824 |
| −30.000 | 0.000 | 0.000 | −0.001 | 0.002 | 0.002 | 0.002 | 0.824 | 0.824 | 0.823 | 0.000 | 0.002 | 0.824 |
| −20.000 | 0.000 | 0.000 | −0.001 | 0.001 | 0.002 | 0.002 | 0.823 | 0.823 | 0.823 | 0.000 | 0.002 | 0.823 |
| −10.000 | −0.002 | −0.001 | −0.001 | 0.000 | 0.002 | 0.001 | 0.828 | 0.827 | 0.828 | −0.001 | 0.001 | 0.828 |
| 0.000 | −0.001 | −0.001 | −0.001 | 0.001 | 0.001 | 0.001 | 0.822 | 0.822 | 0.825 | −0.001 | 0.001 | 0.823 |
| 10.000 | −0.001 | −0.001 | −0.001 | 0.001 | 0.001 | 0.001 | 0.825 | 0.824 | 0.830 | −0.001 | 0.001 | 0.826 |
| 20.000 | −0.001 | −0.001 | −0.002 | 0.001 | 0.000 | 0.001 | 0.826 | 0.819 | 0.823 | −0.001 | 0.001 | 0.823 |
| 30.000 | −0.001 | −0.001 | −0.002 | 0.001 | 0.000 | 0.000 | 0.823 | 0.823 | 0.823 | −0.001 | 0.000 | 0.823 |
| 40.000 | −0.002 | −0.002 | −0.002 | 0.000 | 0.001 | 0.000 | 0.823 | 0.823 | 0.823 | −0.002 | 0.000 | 0.823 |
| 50.000 | −0.002 | −0.001 | −0.002 | 0.000 | 0.001 | 0.001 | 0.822 | 0.823 | 0.822 | −0.002 | 0.001 | 0.822 |
| | | | | | | | Standard Deviation: | | | 0.001 | 0.001 | 0.002 |

Figure 10:
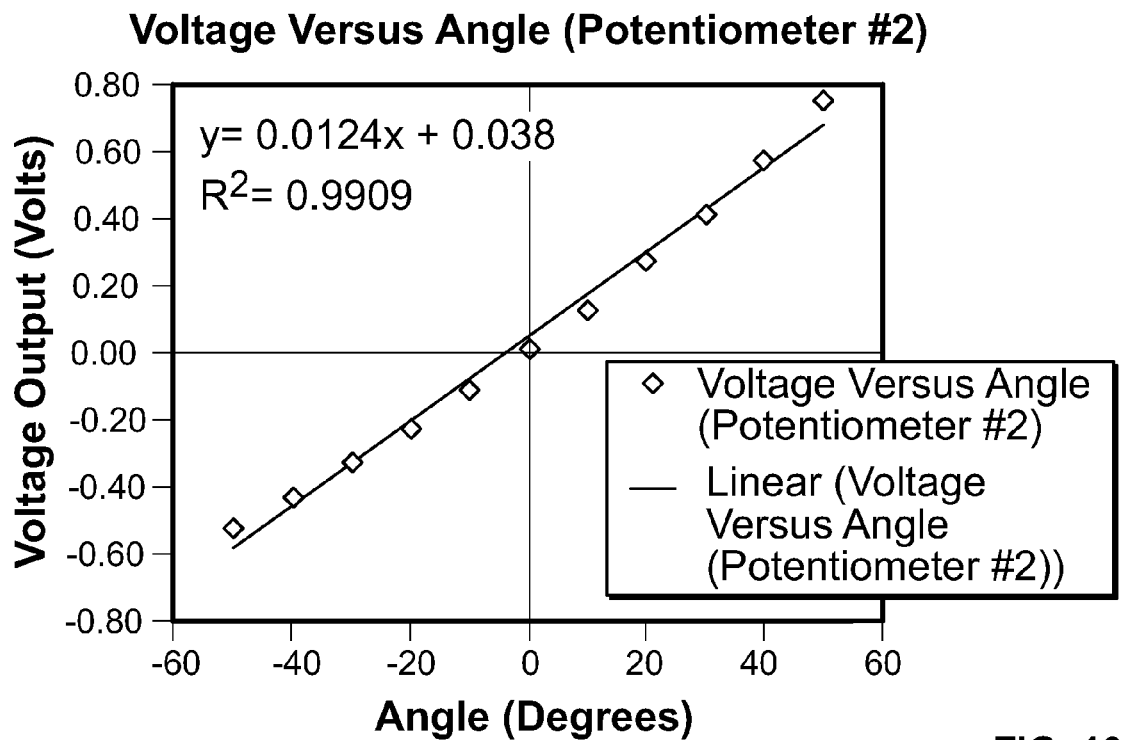
FIG. 10 is graph showing voltage vs. angular displacement for potentiometers used in a goniometer in accordance with an embodiment of the present disclosure.

FIG. 10 is a graph of voltage vs. angular orientation for a potentiometer.

TABLE 3

Potentiometer #2 Voltage Output Results

| Angle Degrees | Voltage Output (Volts) | | | Average | Standard Deviation |
|---|---|---|---|---|---|
| | #1 | #2 | #3 | | |
| −50.000 | −0.527 | −0.526 | −0.527 | −0.527 | 0.001 |
| −40.000 | −0.437 | −0.432 | −0.434 | −0.434 | 0.003 |
| −30.000 | −0.333 | −0.334 | −0.336 | −0.334 | 0.002 |
| −20.000 | −0.231 | −0.232 | −0.233 | −0.232 | 0.001 |
| −10.000 | −0.118 | −0.119 | −0.120 | −0.119 | 0.001 |
| 0.000 | −0.002 | −0.002 | −0.001 | −0.001 | 0.000 |
| 10.000 | 0.118 | 0.118 | 0.118 | 0.118 | 0.000 |
| 20.000 | 0.258 | 0.259 | 0.258 | 0.258 | 0.001 |
| 30.000 | 0.399 | 0.399 | 0.398 | 0.399 | 0.001 |
| 40.000 | 0.558 | 0.557 | 0.558 | 0.558 | 0.001 |
| 50.000 | 0.734 | 0.734 | 0.730 | 0.733 | 0.002 |

TABLE 4

Potentiometer #2 Voltage Output Results Comparing Sensors

| Angle/Linear Displacement | Voltage Output (Volts) | | | | | | | | | Average Sensor 1 | Average Sensor 3 | Average Transducer |
|---|---|---|---|---|---|---|---|---|---|---|---|---|
| | Sensor 1 | | | Sensor 3 | | | Transducer | | | | | |
| | #1 | #2 | #3 | #1 | #2 | #3 | #1 | #2 | #3 | | | |
| −50.000 | −0.001 | −0.001 | −0.001 | 0.001 | 0.001 | 0.001 | 0.824 | 0.824 | 0.821 | −0.001 | 0.001 | 0.823 |
| −40.000 | −0.001 | −0.001 | −0.001 | 0.001 | 0.001 | 0.001 | 0.823 | 0.824 | 0.825 | −0.001 | 0.001 | 0.824 |
| −30.000 | −0.001 | −0.002 | −0.001 | 0.000 | 0.000 | 0.000 | 0.824 | 0.821 | 0.823 | −0.001 | 0.000 | 0.823 |
| −20.000 | −0.001 | −0.002 | −0.001 | 0.000 | 0.001 | 0.002 | 0.824 | 0.823 | 0.824 | −0.001 | 0.001 | 0.824 |

TABLE 4-continued

Potentiometer #2 Voltage Output Results Comparing Sensors

| Angle/Linear Displacement | Voltage Output (Volts) | | | | | | | | | Average Sensor 1 | Average Sensor 3 | Average Transducer |
|---|---|---|---|---|---|---|---|---|---|---|---|---|
| | Sensor 1 | | | Sensor 3 | | | Transducer | | | | | |
| | #1 | #2 | #3 | #1 | #2 | #3 | #1 | #2 | #3 | | | |
| −10.000 | −0.001 | −0.001 | −0.001 | 0.001 | 0.001 | 0.000 | 0.823 | 0.824 | 0.826 | −0.001 | 0.001 | 0.824 |
| 0.000 | −0.002 | −0.002 | −0.002 | 0.001 | 0.001 | 0.001 | 0.824 | 0.824 | 0.821 | −0.002 | 0.001 | 0.823 |
| 10.000 | −0.002 | −0.002 | −0.002 | 0.001 | 0.001 | 0.001 | 0.823 | 0.823 | 0.821 | −0.002 | 0.001 | 0.822 |
| 20.000 | −0.002 | −0.002 | −0.002 | 0.001 | 0.000 | 0.001 | 0.823 | 0.821 | 0.823 | −0.002 | 0.001 | 0.822 |
| 30.000 | −0.002 | −0.002 | −0.002 | 0.001 | 0.000 | 0.001 | 0.824 | 0.823 | 0.823 | −0.002 | 0.001 | 0.823 |
| 40.000 | −0.002 | −0.002 | −0.002 | 0.001 | 0.000 | 0.000 | 0.823 | 0.821 | 0.824 | −0.002 | 0.000 | 0.823 |
| 50.000 | −0.002 | −0.002 | −0.002 | 0.001 | 0.000 | 0.000 | 0.823 | 0.823 | 0.823 | −0.002 | 0.000 | 0.823 |
| | | | | | | | | | Standard Deviation: | 0.000 | 0.000 | 0.001 |

TABLE 5

Potentiometer #3 Voltage Output Results

| Angle Degrees | Voltage Output (Volts) | | | Average | Standard Deviation |
|---|---|---|---|---|---|
| | #1 | #2 | #3 | | |
| −50.000 | −0.515 | −0.518 | −0.519 | −0.517 | 0.002 |
| −40.000 | −0.417 | −0.416 | −0.417 | −0.417 | 0.001 |
| −30.000 | −0.311 | −0.316 | −0.316 | −0.314 | 0.003 |
| −20.000 | −0.216 | −0.216 | −0.217 | −0.216 | 0.001 |
| −10.000 | −0.105 | −0.105 | −0.106 | −0.105 | 0.001 |
| 0.000 | 0.001 | 0.001 | 0.001 | 0.001 | 0.000 |
| 10.000 | 0.139 | 0.138 | 0.136 | 0.138 | 0.002 |
| 20.000 | 0.264 | 0.266 | 0.265 | 0.265 | 0.001 |
| 30.000 | 0.404 | 0.401 | 0.404 | 0.403 | 0.002 |
| 40.000 | 0.562 | 0.569 | 0.569 | 0.567 | 0.004 |
| 50.000 | 0.739 | 0.741 | 0.739 | 0.740 | 0.001 |

TABLE 6

Potentiometer #3 Voltage Output Results Comparing Sensors

| Angle/Linear Displacement | Voltage Output (Volts) | | | | | | | | | Average Sensor 1 | Average Sensor 2 | Average Transducer |
|---|---|---|---|---|---|---|---|---|---|---|---|---|
| | Sensor 1 | | | Sensor 2 | | | Transducer | | | | | |
| | #1 | #2 | #3 | #1 | #2 | #3 | #1 | #2 | #3 | | | |
| −50.000 | 0.001 | 0.001 | 0.001 | 0.001 | 0.001 | 0.001 | 0.823 | 0.821 | 0.823 | 0.001 | 0.001 | 0.822 |
| −40.000 | 0.001 | 0.001 | 0.002 | 0.001 | 0.000 | 0.000 | 0.823 | 0.824 | 0.823 | 0.001 | 0.000 | 0.823 |
| −30.000 | 0.001 | 0.002 | 0.001 | 0.001 | 0.001 | 0.000 | 0.824 | 0.823 | 0.821 | 0.001 | 0.001 | 0.823 |
| −20.000 | 0.001 | 0.001 | 0.001 | 0.000 | 0.001 | 0.000 | 0.823 | 0.824 | 0.824 | 0.001 | 0.000 | 0.824 |
| −10.000 | 0.001 | 0.001 | 0.001 | 0.001 | 0.001 | 0.001 | 0.821 | 0.823 | 0.823 | 0.001 | 0.001 | 0.822 |
| 0.000 | 0.001 | 0.002 | 0.002 | 0.001 | 0.001 | 0.001 | 0.823 | 0.822 | 0.823 | 0.002 | 0.001 | 0.823 |
| 10.000 | 0.001 | 0.000 | 0.002 | 0.001 | 0.001 | 0.001 | 0.823 | 0.823 | 0.821 | 0.001 | 0.001 | 0.822 |
| 20.000 | 0.001 | 0.001 | 0.001 | 0.000 | 0.001 | 0.002 | 0.821 | 0.821 | 0.823 | 0.001 | 0.001 | 0.822 |
| 30.000 | 0.002 | 0.001 | 0.001 | 0.001 | 0.002 | 0.000 | 0.823 | 0.823 | 0.821 | 0.001 | 0.001 | 0.822 |
| 40.000 | 0.001 | 0.001 | 0.002 | 0.001 | 0.002 | 0.001 | 0.824 | 0.823 | 0.823 | 0.001 | 0.001 | 0.823 |
| 50.000 | 0.001 | 0.002 | 0.001 | 0.001 | 0.002 | 0.001 | 0.824 | 0.823 | 0.823 | 0.001 | 0.001 | 0.823 |
| | | | | | | | | | Standard Deviation: | 0.000 | 0.000 | 0.001 |

FIG. 10 shows a graph of voltage vs. angle for potentiometer 14. The sensor output voltages via the Wheatstone bridge were recorded versus a known angle and subjected to linear regression analysis, yielding the slope and intercept. Repeated calibrations and subsequent average of the regression parameters permitted a reproducible and simple scaling of the output voltages to yield physical values of angle. Linear Data Analysis was performed on the 10 data points for each test performed. The data points represent the minimum and maximum angles of rotational measurements. The statistical analysis of the data was performed. Linear regression found the $R^2$ value >0.9909. Standard deviation was found to be <0.008 volts. The slope comparison between each potentiometer shows no significant difference. The graphical results can be used as a reference to convert the voltage output into a linear displacement/angle measurement. Similar graphing was done for potentiometers 12 and 16 with similar results.

Figure 11:
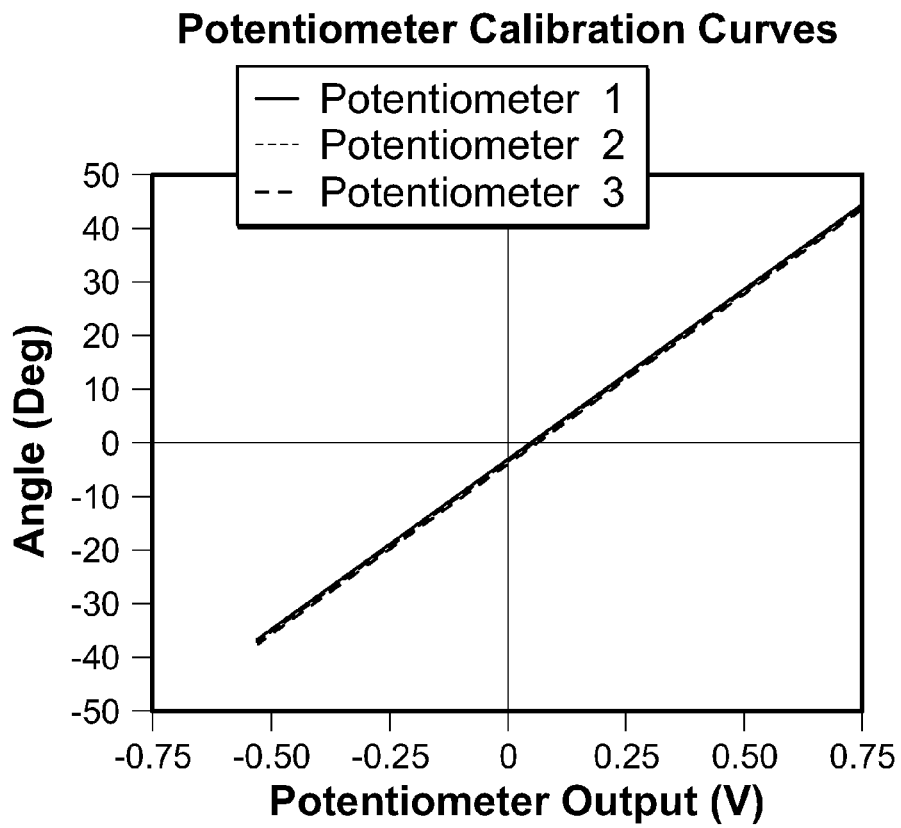
FIG. 11 is a graph showing an exemplary calibration curve for a potentiometer used in a goniometer in accordance with an embodiment of the present disclosure.

FIG. 11 shows a potentiometer calibration curve for each of the potentiometers 12, 14, 16. Because the curves are near identical, the curves overlap to the degree that only one line is visible at this level of resolution.

Figure 12:
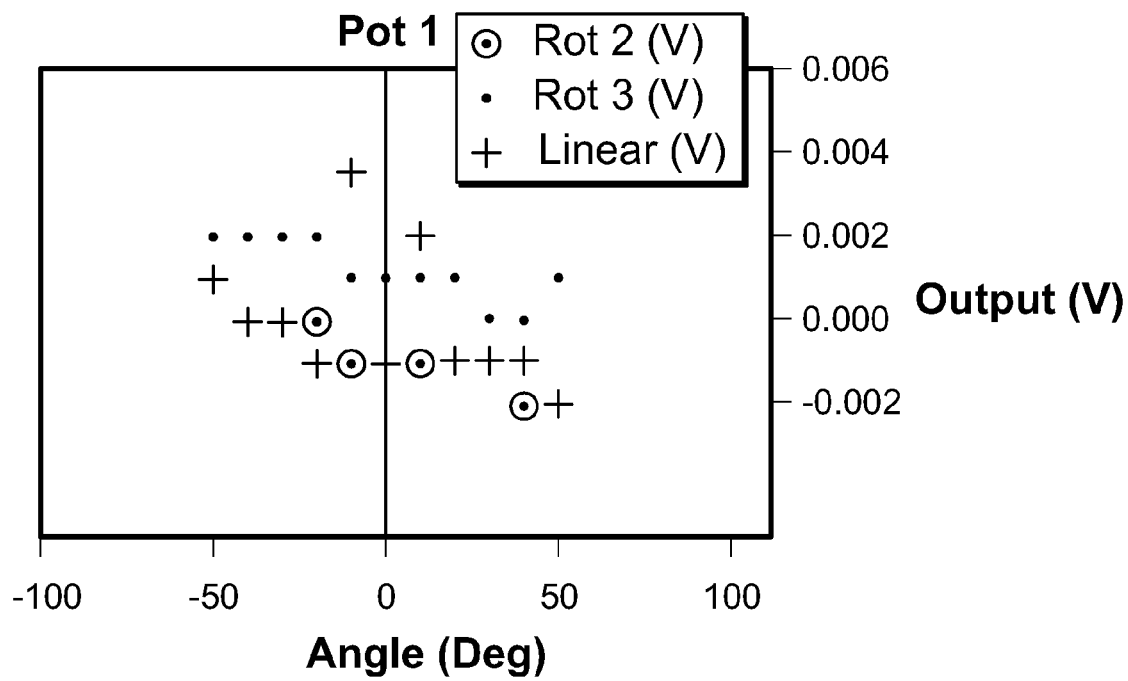
FIG. 12 is a graph showing cross-talk readings for a goniometer in accordance with an embodiment of the present disclosure. This data is attributable to the operation of potentiometers and a transducer.

After each of the potentiometers and the transducer was calibrated, an analysis was conducted of each sensor moving individually while maintaining the other stationary in order to determine the effect of crosstalk between the potentiometers and transducer from preset output voltages. The sensors in the device were connected to a single circuit board with multiple Wheatstone bridge circuits. As each potentiometer was rotated, the crosstalk results were recorded. When the transducer was displaced, the crosstalk results were recorded as well. Between each trial, the sensors were returned to zero output voltage. The crosstalk result between sensors was found to be <0.2 degrees. FIG. 12 is a graph of cross-talk results for each of the potentiometers 12, 14, 16 and the transducer 24.

Prior to use, the linear transducer was calibrated so as to permit direct measurement of changes in extension from the output. The transducer in the device was connected, along with the potentiometers, to a single circuit board with multiple Wheatstone bridge circuits. Upon displacement of the transducer 24, an electrical signal was generated in its respective bridge due to the unbalancing of the circuit.

TABLE 7

Transducer Voltage Output Results

| | Voltage Output (Volts) | | | | Standard |
|---|---|---|---|---|---|
| Distance (mm) | Trial #1 | Trial #2 | Trial #3 | Average | Deviation |
| −6.000 | 1.404 | 1.408 | 1.406 | 1.406 | 0.002 |
| −3.000 | 1.608 | 1.614 | 1.609 | 1.610 | 0.003 |
| 0.000 | 1.716 | 1.710 | 1.711 | 1.712 | 0.003 |
| 3.000 | 1.816 | 1.814 | 1.814 | 1.815 | 0.001 |
| 6.000 | 1.935 | 1.934 | 1.921 | 1.930 | 0.008 |

Figure 13:
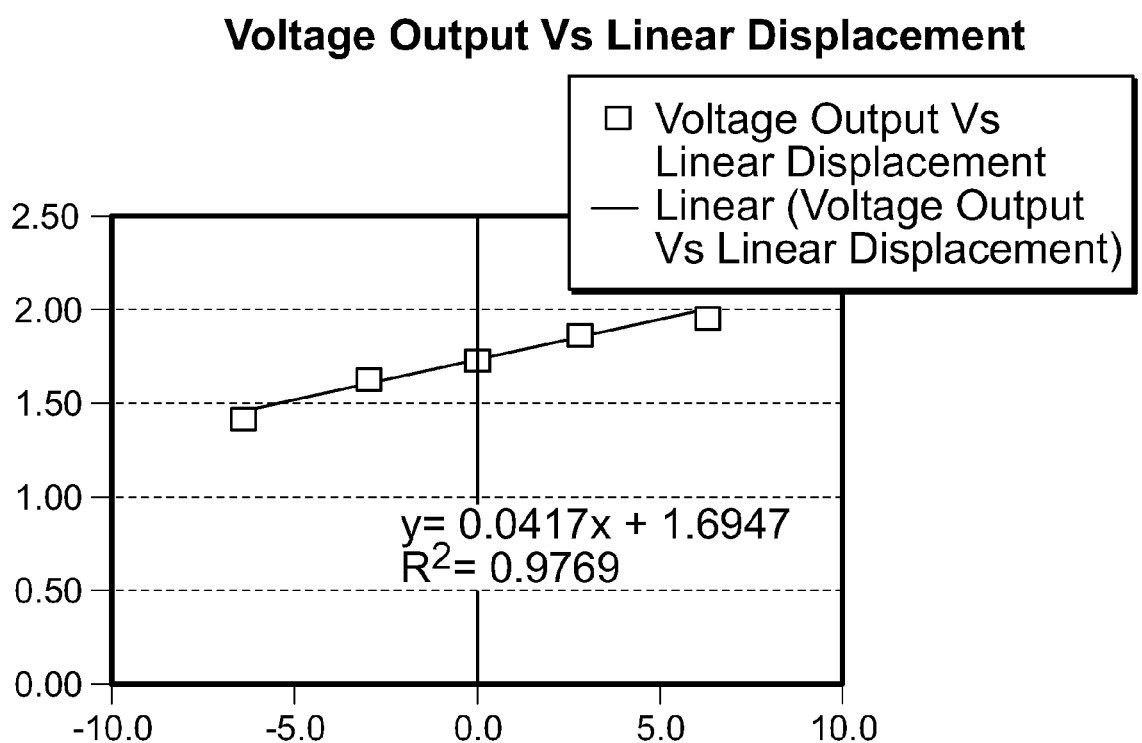
FIG. 13 is a graph showing voltage output vs. linear displacement for a transducer used in a goniometer in accordance with an embodiment of the present disclosure.

The sensor output voltages via the Wheatstone bridge were recorded for known linear extension values versus the respective output voltage yielding the slope and intercept. Repeated calibrations and subsequent average of the regression parameters permitted a reproducible and simple scaling of the output voltages to yield physical values of extension. Linear Data Analysis was performed on the 5 data points for the test performed. A statistical analysis of the data was performed. Linear regression found the $R^2$ value=0.9769, as shown in FIG. 13.

Figure 14:
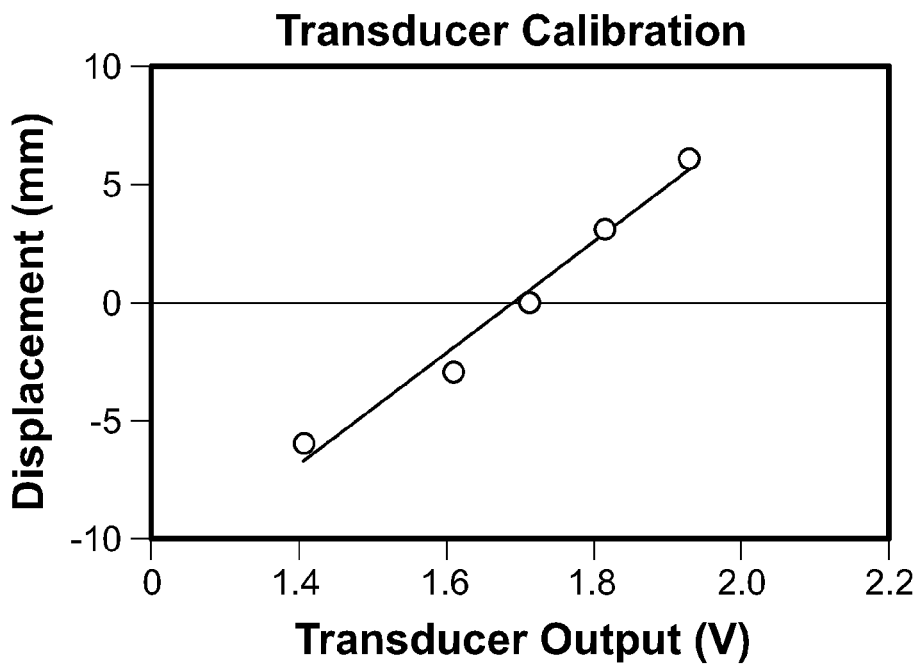
FIG. 14 is a graph showing an exemplary calibration curve for a transducer used in a goniometer in accordance with an embodiment of the present disclosure.

FIG. 14 shows a graph of the transducer 24 calibration.

The stability of each calibrated sensor was assessed through the drift test. Drift was validated over time intervals. The purpose of this test was to verify if drift is to be taken into consideration for sensor output analysis. Over time, the result of Drift between sensors was found to be <0.000043 degrees. Drift was negligible and was not a significant factor in interpreting results. The test determined that drift did not compromise the integrity of the sensors.

Figure 15:
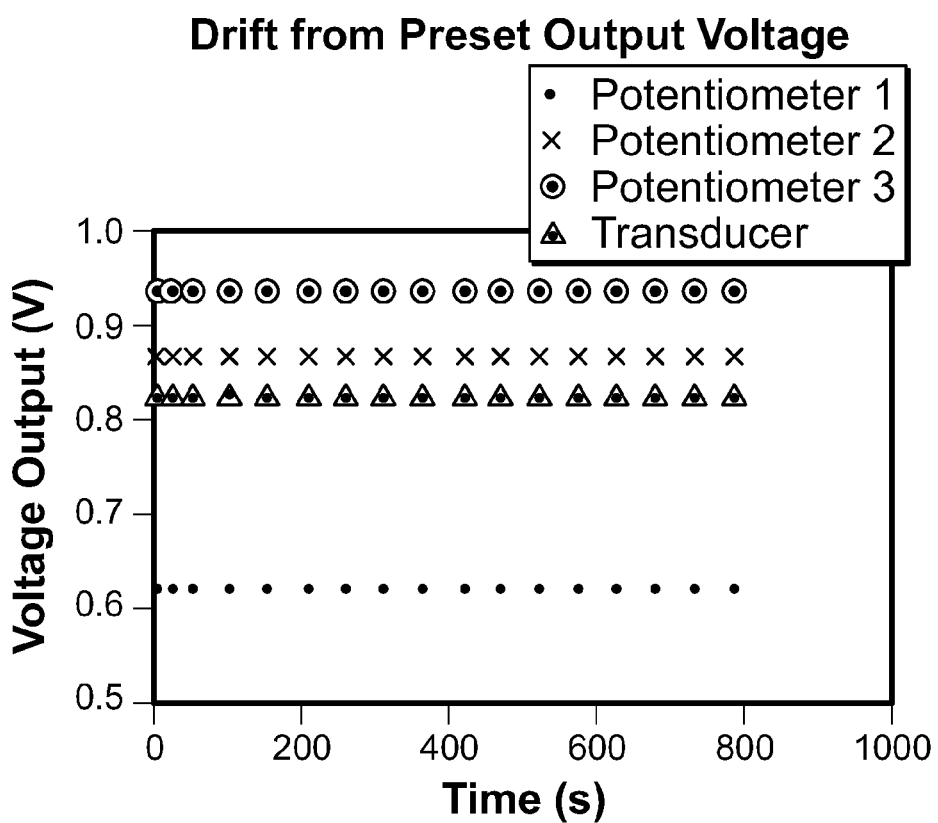
FIG. 15 is a graph showing drift in voltage output for potentiometers and a transducer used in a goniometer in accordance with an embodiment of the present disclosure.

FIG. 15 shows a graph of drift from preset output voltage for each of the potentiometers 12, 14, 16 and the transducer 24. In each case, drift is negligible.

FIG. 16 shows an alternative embodiment of the present disclosure. The goniometer 110 has potentiometers 112, 114, 116, (112 and 116 shown only by the stem thereof for ease of illustration, but which would be the same as 114) which would be commercially available, for example, Vishay/Spectrol potentiometers from Vishay, Inc of Shelton, Conn. The potentiometers 112, 114, 116 may be used to measure rotary motion along three axes intersecting at an intersection-point, as in the goniometer 10 described above. The potentiometers 112, 114 and 116 are mounted in three flanges 118, 120, 122, respectively, and are used to couple the flanges together into an articulable assembly. The flanges 118, 120, 122 have recesses 109 that are adapted to accept the top of the threaded nipples N of the potentiometers 118, 120, 122, respectively, either threadedly or in a slip fit arrangement. A mounting plate 107, by which it may be coupled to flanges 118, 120, 122, is retained by screws 111. A benefit to this arrangement is that the housing H of the potentiometer may be position at any rotary orientation and then tightened into the flange, e.g., 120 via the mounting plate 107. A lock nut 107a (see FIG. 5) may be employed to secure the potentiometer at a given orientation relative to the mounting plate 107 and/or flange.

FIG. 16 illustrates a similar construction as that described above for of coupling the flanges 118, 120 122 to each other via the potentiometers 112, 114, 116, with 118 and 120 being coupled via a coupling cylinder 121.

The goniometer 110 does not include a linear displacement sensor/transducer 24, and the top rod 126 extends from the upper L-shaped flange 120 to a terminal fitting 115 that couples to the plate 134. As before, a harness 30 would be attached to the plate 134 and a harness 40 would attach to attachment plate 144, which in the embodiment shown, has a clamp plate 144c fastened thereto by screws that may be tightened to capture the belt portion 40a therebetween. The attachment plate 144 is coupled to the bottom U-shaped flange 122 via a bottom rod 126, which may be a threaded rod that threads into the attachment plate 144 and the flange 122. Alternatively, the bottom rod 126 may be welded, cast/molded or glued in conjunction with the plate 144 and/or the flange 122. With respect to the attachment to an interpreter 52 and computer, the goniometer 110 will be attached in the same way as the goniometer 10 (except for the lack of a transducer 24) and will operate in the same fashion as described above.

An aspect of the present disclosure is that the measurement of the angles of the anatomy as it moves not only can identify and record such angles at the endpoints of motion, but can record the angles as the motion occurs at a high sampling rate throughout the entire motion path. The recoded data may be used to identify movement patterns that may be indicative of specific conditions of the joint(s)/moving anatomical structures under review. For example, it has been observed that the ranges and rates of motion, as well as the patterns of motion, e.g., retrograde or periodic motions at given motion thresholds associated with volitional motion differ from those imposed by involuntary response to pain or simply not being able to move any further. These motion patterns may be used to detect the impact of the psychology or motive of the patient in moving in a certain way, e.g., motion controlled by a patient's fear or by duplicity, such as may be encountered in a patient who is attempting to simulate an injured state that is not present in order to assert a false claim of injury or disease state for a claim of damages, disability or to support a fraudulent insurance claim. In the converse, actual injury may be supported by an analysis rendered by a goniometric system in accordance with the present disclosure. The goniometer 10 may generate output data while the anatomy is moved volitionally or by another, such as by a therapist and different patterns may be observed under these different conditions.

An aspect of the present disclosure is the fact that the potentiometers, being arranged in an x,y,z, axis system, may capture motion on a plurality of axes simultaneously. This may be beneficial in analyzing the motion of a joint having coupled motions, i.e., a plurality of motions along different axes that occur simultaneously. The spine provides an example of an anatomy having a complex matrix of coupled motions, which will differ for patients with different conditions. For example, a person with scoliosis when bending from a straight position to a forwardly bent position will also execute spinal rotation and sideways bending as a consequence of bending in the forward direction. The goniometric system of the present disclosure allows a motion profile along multiple axes to be recorded for analysis, review and comparison to later motion profiles of the same person, e.g., during a recuperative period or during the progression of a disease, or compared to other persons having similar conditions or to a population of persons having healthy joints.

In accordance with one embodiment of the present disclosure, the output of the goniometric system of the present disclosure is conveyed wirelessly from a transmitter attached to the patient to a remote receiver.

In accordance with another embodiment of the present disclosure, the goniometric data is conveyed to a computer that is connected to the internet and linked by an internet connection to a remote computer in the office of a physician or therapist who can observe and analyze the data to asses the patient remotely. In another embodiment, the goniometric system conveys the data to a cell phone or other wireless devices for transmission via a wireless network.

The goniometer of the present disclosure may be used in lieu of x-rays to measure and analyze the motion of an anatomy, e.g., human spinal motion. The goniometer 10 ensures that the angular rotations associated with the spinal range of motion. It yields immediate results in an office setting and observes and records dynamic and simultaneous motion about three axes. The coincident axial alignment of the axes A-A, B-B, and C-C at the intersection point 36 reduces excessive computations to determine the patient full specific range of motion. It should be noted that the present disclosure can have numerous modifications and variations. For instance, in another embodiment, a goniometer is capable to taking measurements of motion of other joints such as the hip, knee, shoulder, and wrist by modifying and incorporating appropriate mounting mechanism (e.g., harnesses, band, clamps). It will be understood that the embodiments described herein are merely exemplary and that a person skilled in the art may make many variations and modifications without departing from the spirit and scope of the present disclosure All such variations and modifications are intended to be included within the scope of the present application.

We claim:

1. A device for measuring movement of a body having a first point that is moveable relative to a second point, comprising:
    three articulable elements and an intermediate member, a first articulable element mechanically and pivotally coupled to a second articulable element defining a first axis of rotation, the second articulable element mechanically and pivotally coupled to the intermediate element defining a second axis of rotation, the third articulable element connected to the intermediate member defining a third axis of rotation, the second axis being perpendicular to the first axis and the third axis being perpendicular to the second axis, each of the first second and third axes intersecting each of the other of the first, second and third axes, the three pivotally connected articulable elements defining an articulable assembly;
    a sensor coupled to each of the three articulable elements and capable of sensing rotation thereof relative to an adjacent articulable element and generating a first signal representative of the angle of rotation;
    a computer capable of receiving a signal corresponding to the first signal and storing the angle of rotation;
    a first end of the articulable assembly capable of coupling proximate the first point on the body;
    a second end of the articulable assembly capable of coupling proximate to the second point on the body.

2. The device of claim 1, wherein the rotation of any of the articulable elements on the three axes is independent of the rotation of any other of the articulable elements, except when in a condition of gimbal lock.

3. The device of claim 2, wherein the articulable assembly is capable of simultaneous independent movement of each of the plurality of articulable elements when moved by the body, generating a plurality of independent signals attributable to rotation about the three axes.

4. The device of claim 1, wherein the sensors are potentiometers.

5. The device of claim 4, wherein the potentiometers each have a stem rotatable relative to a housing thereof, the potentiometers forming the mechanical link between adjacent elements in the articulable assembly upon which the adjacent elements pivot, with the stem attached to a first of the adjacent elements and the housing attached to a second of the adjacent elements, the potentiometers capable of generating the first signal when rotated.

6. The device of claim 5, further comprising an interpreter capable of receiving the first signal, converting it to a digital signal and conveying the digital signal to the computer.

7. The device of claim 6 wherein the interpreter includes a Wheatstone bridge for determining a resistance value of the potentiometer at a given rotational position of the potentiometer.

8. The device of claim 6, wherein the computer has a program running therein capable of converting the digital signal into rotational angle data corresponding to the rotation of the articulable elements and communicating the angle data to a user.

9. The device of claim 8, further comprising a phone interface through which the angle data is capable of being communicated to another computer over a wireless network.

10. The device of claim 8, wherein the angle data stored in the computer is obtained over a period of time at a given sampling rate, such that multiple angle data values are generated and stored when the body executes a motion from a first position to a second position.

11. The device of claim 10, further comprising a first extension with a first end coupled to the first end of the articulable assembly and a second end capable of being coupled to the body proximate the first point and a second extension with a first end coupled to the second end of the articulable assembly and a second end capable of being coupled to the body proximate the second point.

12. The device of claim 11, wherein the first articulable element includes a U-shaped flange and the second and third articulable elements are each L-shaped flanges, a first potentiometer attached to a first arm of the U shape by the housing thereof with the stem thereof extending toward and being mechanically coupled to a first arm of the L-shaped flange of the second articulable element, a second potentiometer attached to a second arm of the L shaped flange of the second articulable element with the stem thereof extending toward and mechanically coupled to the intermediate member, a third potentiometer attached to a first arm of the L shaped flange of the third articulable element with the stem thereof extending toward and mechanically coupled to the coupling at right angles to the stem of the second potentiometer, the first end of the first extension attached to the U-shaped flange at a second arm opposite to the first potentiometer and the first end of the second extension attached to the second L-shaped flange on a second arm of the second L-shaped flange, the second ends of the first and second extensions capable of being coupled to a harness worn on the body.

13. The device of claim 1, further comprising a wireless connection between the device and the computer.

14. The device of claim 1, wherein the computer is connected to the Internet and is capable of communicating the signal data to a remote computer.

15. The device of claim 1, further comprising a linear transducer coupled between the articulable assembly and the first point on the body and capable of generating a signal representative of a change in length between the first point and the second point on the body when the body is moved.

16. A method of measuring the movement of an articulable anatomy moveable from a first position to a second position, comprising the steps of:
(A) obtaining a device in accordance with the device of claim 1;
(B) coupling the device to the anatomy, with the device bridging from a first point on the anatomy to a second point on the anatomy, such that when the anatomy moves, the first point moves relative to the second point and moves the articulable elements in a manner corresponding to the movement of the anatomy, the sensors generating virtually simultaneous, independent signals corresponding to each rotational movement of the articulable elements without cross-talk between the articulable elements;
converting the independent signals into angle data representing the magnitude of rotation sensed by each sensor; and
recording the angle data for a plurality of movement states from a start position of the anatomy to an end position.

17. The method of claim 16, further comprising the step of comparing the angle information to angle information previously obtained during the motion of a comparable anatomy.

18. The method of claim 16, wherein the anatomy is a spine.

19. The method of claim 16, wherein the anatomy is an articulable appendage.

20. The method of claim 16, wherein the measuring is conducted to assess the functionality of the anatomy and includes the step of comparing a first set of angle data associated with the anatomy to a second set of angle data associated with a comparable anatomy executing a similar motion pattern at an earlier time.

21. The method of claim 20, wherein the comparable anatomy is the anatomy of the same individual.

22. The method of claim 20, wherein the comparable anatomy is the anatomy of at least one other individual.

* * * * *